US00PP10787P

United States Patent [19]

Hill, Jr.

[11] Patent Number: Plant 10,787

[45] Date of Patent: Feb. 9, 1999

[54] GUZMANIA PLANT NAMED 'OLYMPIC'

[75] Inventor: Herbert H. Hill, Jr., Lithia, Fla.

[73] Assignee: Twyford International, Inc., Santa Paula, Calif.

[21] Appl. No.: 877,956

[22] Filed: Jun. 18, 1997

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 9,426 1/1996 Bak et al. ..... Plt./88.8

*Primary Examiner*—James R. Feyrer

*Assistant Examiner*—Kent L. Bell

*Attorney, Agent, or Firm*—Foley & Lardner

[57] ABSTRACT

A new cultivar of Guzmania named 'Olympic' having a very long lasting yellow and red bracted inflorescence. The inflorescence is clean appearing, and does not appear "flowered out" with age. The foliage is very dark green, shiny, durable and resistant to leaf spotting and tip browning. Plants of 'Olympic' tolerate a wide range of cultural conditions and are easy to grow.

2 Drawing Sheets

The present invention relates to a new and distinct cultivar of Guzmania, a genus within the family bromeliaceae, hereinafter referred to by the cultivar name 'Olympic'. The new cultivar is an interspecific hybrid resulting from a cross identified below.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, and the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Olympic' is the product of a planned breeding program and was originated by the inventor Herbert H. Hill in Lithia, Fla. from a cross made during such program in May 1989. The female, or seed parent is *Guzmania conifera* 'Yellow'. The male or pollen parent, is *Guzmania lingulata* c.v. 'Superb'. The selection comprising the new variety was chosen after commencement of flowering in May 1992. The new cultivar was asexually propagated by off-shoots by the inventor in Lithia, Fla. beginning in November 1992. Asexual propagation by tissue culture was initiated in October 1994. Continuous asexual propagation has demonstrated that the combination of characteristics as herein disclosed for the new cultivar 'Olympic' are firmly fixed and are retained through successive generations of asexual reproduction.

Guzmania 'Olympic' is particularly characterized by the following.

1. The inflorescence produced by 'Olympic' has bright yellow bracts which are flushed with red.

2. The foliage of 'Olympic' is dark olive green and shiny, and is resistant to leaf tip browning and leaf spotting. The foliage is leathery and resistant to damage from handling and shipping.

3. The inflorescence of 'Olympic' is very long lasting, and can remain attractive with good color for as long as six months indoors.

4. The flowers do not emerge completely from under the primary bracts, and the spent flowers are not visible. The inflorescence of 'Olympic' is clean appearing, and does not appear 'flowered out'.

Perhaps the closest comparison cultivar is Guzmania 'Torch', disclosed in U.S. Plant Pat. No. 9,426. 'Torch' is particularly characterized by its unusual bright red and yellow inflorescence. Compared to 'Torch', the floral bracts of 'Olympic' are primarily yellow, flushed with red at the base. In addition, the leaves of 'Olympic' are narrower and a more uniformly darker green than those of 'Torch'.

Guzmania 'Olympic' has not been tested under all available environmental conditions. The phenotype may vary with variations in environmental conditions such as temperature, light intensity, day length and humidity without, however, any variance in genotype.

The accompanying color photographic drawings show typical characteristics of Olympic, with colors being as true as possible with illustrations of this type.

The photo on sheet 1 shows a 14 month old plant of 'Olympic' grown from an off-shoot, and finished in a 20 cm pot.

The photo on sheet 2 shows close up detail of an inflorescence of 'Olympic'.

The following description is based on the plant illustrated in the photographic drawings. The plant was grown in Lithia, Fla. by the inventor in greenhouse conditions which are typical for the industry. Color references are made to The Royal Horticultural Society Colour chart (R.H.S.).

I. Plant:

*Form/growth habit.*—Basal rosette of closely layered strap-like leaves arranged around a short central stem.

*Height.*—Approximately 46 cm–50 cm including inflorescence.

*Diameter.*—Approximately 74 cm–80 cm.

II. Foliage:

*Size of leaf.*—The basal leaves are approximately 50–55 cm long, and 3.7–4.6 cm wide (flattened). At their widest point near the base, the leaves are approximately 7.5 cm to 8.4 cm wide.

*Shape of leaf.*—The leaf blade is ligulate with an acute tip. The leaf blade is channeled. The margins are entire. The leaves are curved outward over their length.

*Surface texture.*—The leaf blade is stiff and leathery, with a shiny surface.

*Color.*—The leaves are dark green throughout the foliage. The adaxial surface is much darker and greener than but closest to 137 A, and the abaxial surface is greener than but closest to 147 A. The leaves are frequently striated with 187 B near their base.

*Average number of leaves.*—The plant produces approximately 19 leaves before producing an inflorescence.

*Roots.*—Roots greenish white, changing to brown, wiry with fine laterals.

III. Bracts:

*Dimensions and color.*—The terminal bracts with underlying flowers are approximately 5.0–5.7 cm long, and approximately 1.2 cm to 1.5 cm wide. The adaxial and abaxial surfaces are yellow 14 A-B flushed with red 44 A, 45 B centrally and marginally. The primary bracts are approximately 6.3 cm to 7.2 cm long and 2.0 cm to 2.8 cm wide. The abaxial and adaxial surfaces are 45 A-B, with the uppermost primary bracts being striated with 14 A. The tips of the primary bracts are anthocyanous 183 A in color. The scape bracts are approximately 10.5 cm to 26 cm long, and approximately 2.5 cm to 4.5 cm wide.

The scape bracts diminish in length and become marginally tinged with color ascending the scape. The adaxial surface of the scape bracts is darker and greener than, but closest to 137 A.

The abaxial and adaxial margins of the upper scape bracts are 45 A-B. The area of the margin covered with 45 A-B increases on the upper scape bracts. The abaxial surface is darker than but closest to 137 B.

*General shape and arrangement.*—The terminal bracts are lanceolate to elliptic with acute tips, arranged in very closely spaced vertical ranks along the inflorescence. The uppermost terminal, and primary bracts are very closely spaced, less than 1.0 to 3 mm apart.

The inflorescence is approximately 9 cm to 12 cm in width, and 11 cm to 13 cm in height. The primary bracts are lanceolate to elliptic in shape with cuspidate tips. The scape bracts are ligulate with acute to cuspidate tips. The scape bracts clasp the scape, and are spaced approximately 16–25 mm apart.

*Number.*—Terminal Bracts: approximately 157. Primary Bracts: approximately 9. Scape Bracts: approximately 19.

*Texture.*—Leathery, with a shiny surface.

*Margin.*—Entire.

*Scape.*—The scape is approximately 34 cm tall, approximately 11 mm in diameter, and 145 B-C in color.

IV. Branch spikes: The inflorescence may contain branch spikes which protrude from under primary bracts, each containing approximately 20 flowers. Branch spikes are typically present on larger plants, in 20 cm pots, and absent on smaller plants. The bracts of the branch spikes are similar in color and dimension to the terminal bracts.

V. Flowers:

*Borne.*—Terminal in the inflorescence, and in branch spikes.

*Individual flowers.*—Approximately 150 flowers or flower buds present, terminal in the inflorescence concealed under bracts. Calyx. — Gamosepalous, three sepals present approximately 1.8 cm long and 0.4 cm wide, yellow 6 C-D in color. Corolla. — Gamopetalous, three petals present approximately 3.0 cm to 3.5 cm long and 0.5 cm wide, yellow 13 B-C in color.

*Time of blooming.*—In mature plants, flowering begins approximately 13–16 weeks after induction, at any time of the year.

*Duration of inflorescence.*—The inflorescence will hold its color approximately 6–12 months. Individual flowers last 1 day, and the total duration of flowering is about 6 weeks.

VI. Floral organs:

*Ovary.*—Superior, three locules, 9 mm long, 145 D in color.

*Style.*—3.0 cm long, 5 C in color, 150 B at tip.

*Stamens.*—Six present, filament 2.9 cm long, anthers 8 mm long, 4 D in color.

VII. Seed characteristics: Sterile F1 hybrid.

It is claimed:

1. A new and distinct cultivar of Guzmania plant named 'Olympic', as illustrated and described.

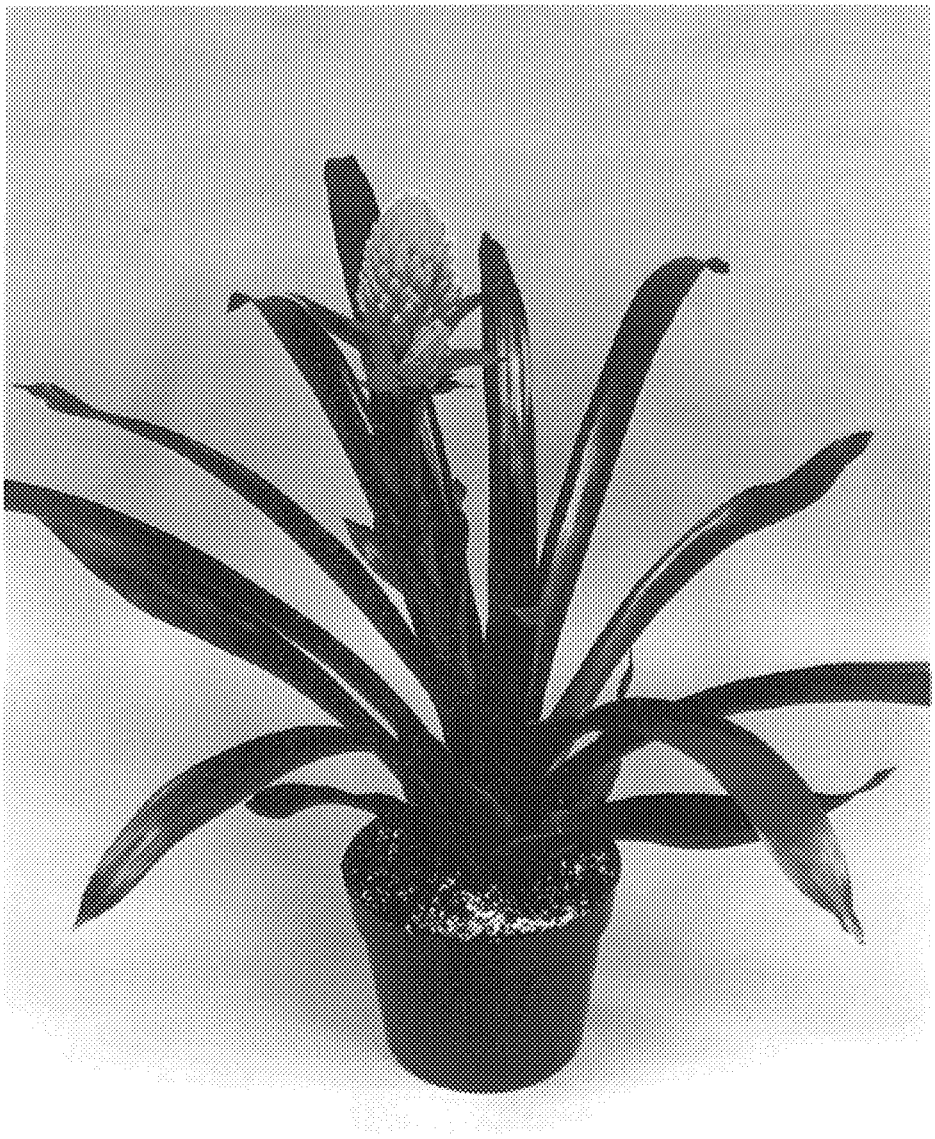

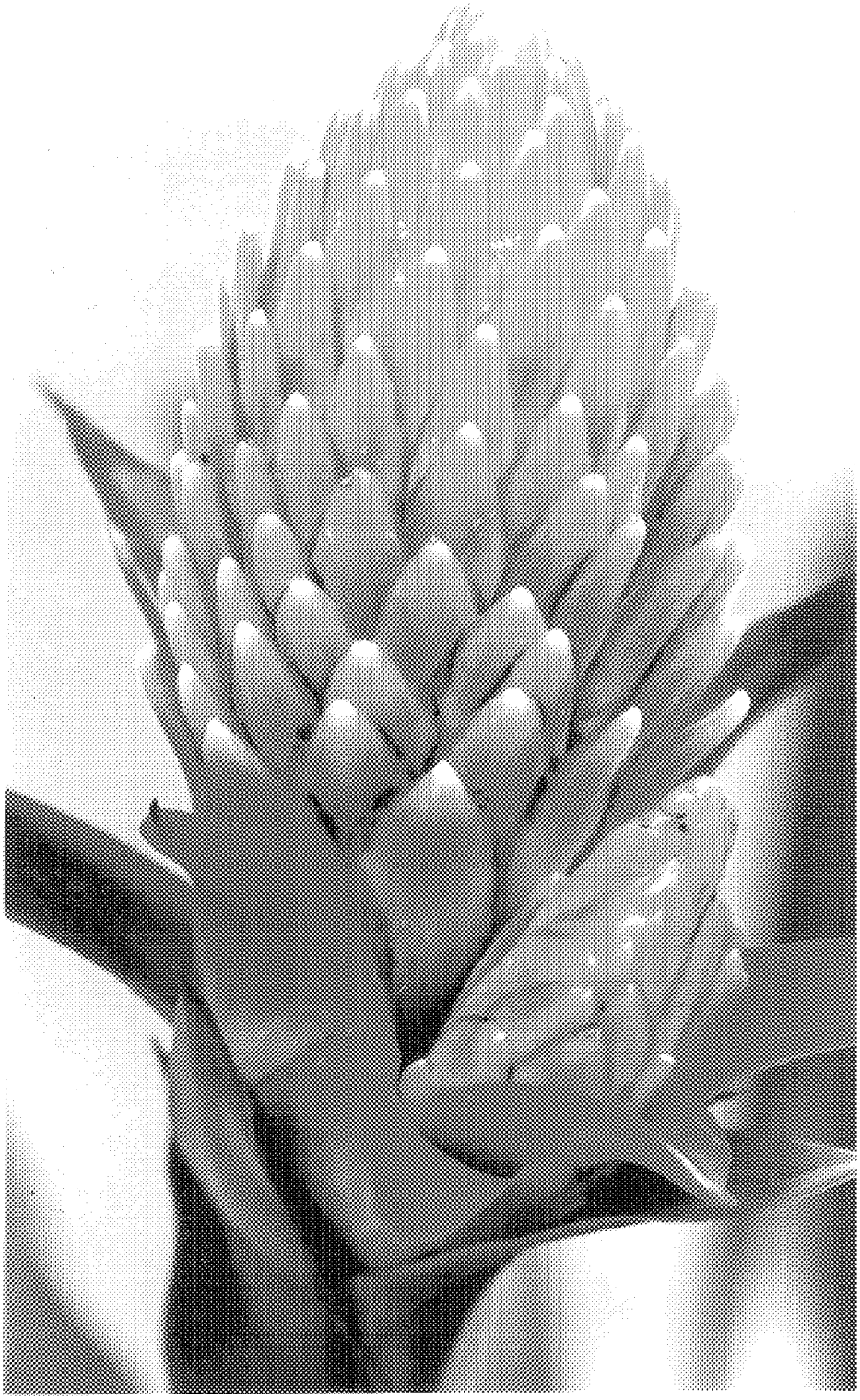

* * * * *